(12) United States Patent
Grassmann et al.

(10) Patent No.: US 7,409,041 B2
(45) Date of Patent: Aug. 5, 2008

(54) METHODS OF TRANSMISSION MODE X-RAY DIFFRACTION ANALYSIS AND APPARATUSES THEREFOR

(75) Inventors: Olaf Grassmann, Kandern (DE); Michael Hennig, Weil am Rhein (DE); Remo Anton Hochstrasser, Oberwil (CH); Urs Schwitter, Reinach (CH)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 11/416,220

(22) Filed: May 2, 2006

(65) Prior Publication Data

US 2006/0245544 A1 Nov. 2, 2006

(30) Foreign Application Priority Data

May 2, 2005 (EP) .................................. 05076024

(51) Int. Cl.
*G01N 23/20* (2006.01)
(52) U.S. Cl. ........................................... 378/79; 378/71
(58) Field of Classification Search .............. 378/70–90
See application file for complete search history.

(56) References Cited

U.S. PATENT DOCUMENTS 6,163,592 A * 12/2000 He et al. ........................ 378/71
6,388,262 B1 * 5/2002 Alani et al. ............. 250/442.11
2004/0208284 A1 * 10/2004 Brugemann et al. ........... 378/70
2005/0002487 A1 1/2005 Blomsma et al.

FOREIGN PATENT DOCUMENTS

EP           1376108 A2      1/2004
WO     WO 03081221 A2      10/2003

* cited by examiner

*Primary Examiner*—Courtney Thomas
(74) *Attorney, Agent, or Firm*—George W. Johnston; John P. Parise; Karen J. Ghinculov

(57) ABSTRACT

Methods for transmission mode X-ray diffraction analysis of a sample by means of apparatuses comprising an X-ray radiation source that provides X-ray radiation for irradiating the sample and a detector for detecting X-ray radiation transmitted through and diffracted by the sample. The methods include: (a) placing a sample to be analyzed on a substrate, (b) generating X-ray radiation by means of an X-ray radiation source, (c) positioning the substrate and the sample in an initial position, (d) rotating the substrate and the sample with respect to the initial position around a rotation axis over a predetermined rotation angle, (e) tilting the substrate and the sample with respect to the initial position around a tilting axis over a tilting angle, (f) detecting with a detector the X-ray radiation transmitted through and diffracted by the sample during a time interval, and (g) analyzing the X-ray radiation that is detected.

50 Claims, 12 Drawing Sheets

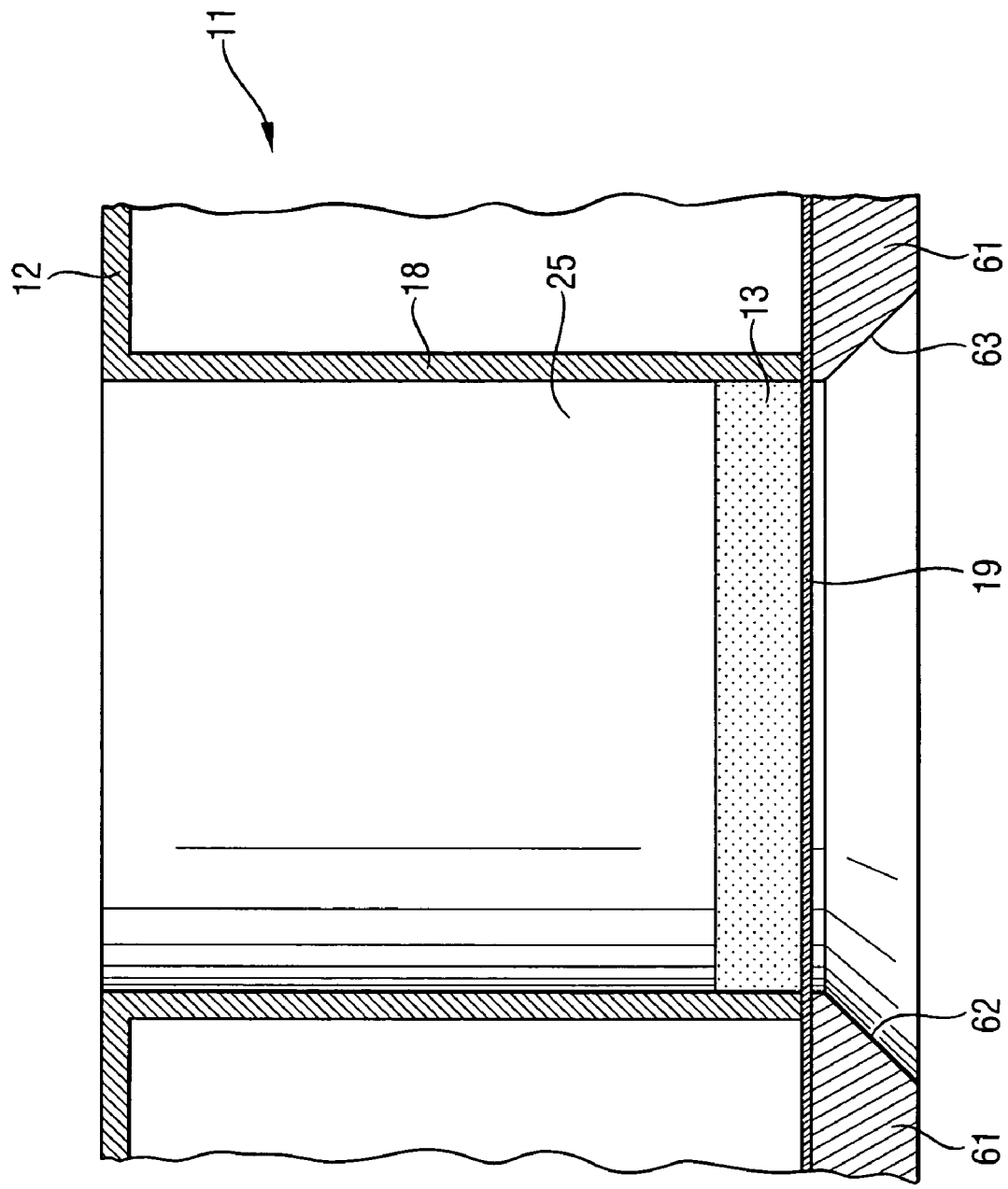

METHODS OF TRANSMISSION MODE X-RAY DIFFRACTION ANALYSIS AND APPARATUSES THEREFOR

FIELD OF THE INVENTION

Methods and apparatuses for transmission mode X-ray diffraction analysis.

BACKGROUND OF THE INVENTION

Combinatorial chemistry refers to techniques to fabricate, test, and store the resulting data of a material library containing tens, hundreds or even thousands of different materials or compounds. Combinatorial investigations require rapid screening techniques to test and evaluate variations of composition, structure and property within a material library. X-ray diffraction analysis is one of the most suitable screening techniques of solid state properties because abundant information can be revealed from the diffraction pattern, and X-ray diffraction analysis is fast and non-destructive.

Diffraction pattern analysis plays an important role in such diverse applications as solving molecular structures, identifying compounds, and fabricating materials. If a compound can be crystallized into sizeable crystals, diffraction patterns from single crystals can provide information about the crystal structure of the compound. Many compounds, however, can only be obtained as powders. Although a powder diffraction pattern yields much less information than that generated by a single crystal, it is unique to each substance with a particular crystal structure, and is therefore highly useful for purposes of identification.

Scattering of incident X-ray radiation from a sample of material can yield information about the atomic structure of the material. When such a beam of radiation strikes a sample, a pattern of diffracted radiation is created, which has a spatial intensity distribution that depends on the wavelength of the incident radiation and the atomic structure of the material. The spatial intensity distribution can be recorded on a suitable detector such as a point detector, a 1D detector or a 2D detector. Diffraction analysis is a method of studying crystalline materials, crystallization behavior, and liquid, gel or solid phase, or phase transitions of materials.

In certain circumstances, it is desirable to perform a sample analysis using transmission mode X-ray diffraction analysis for various reasons, including the need for low angle diffraction, and advantages when testing thin samples or samples in liquid environments.

A problem that is encountered with known powder diffraction analysis equipment using a 2D detector is that during detection of the diffraction radiation, single diffraction spots and arcs are often observed instead of rings, especially when organic crystalline material (such as pharmaceuticals) is irradiated. This may result from the fact that not all lattice planes of the crystalline powder material have or have not been exposed to X-ray radiation for the same time or the same amount, because the crystals were not random oriented or only a few crystals were present. As a result, the peak intensities of the powder diffraction patterns recorded with a point or a 1D detector (one-dimensional detector) are not correct, and no representative 1D-powder diffraction pattern (intensity vs. diffraction angle 2θ.) is created. This causes problems during comparison of diffraction patterns for identification.

SUMMARY OF THE INVENTION

A method of transmission mode X-ray diffraction analysis includes the following steps. A sample to be analyzed is placed on a substrate that is transparent to X-ray radiation and that is adapted for receiving and holding the sample. X-ray radiation is generated by means of an X-ray radiation source that generates a strip-shaped X-ray beam with a central part that extends along a path in a plane. The substrate and the sample are placed in an initial position in which the sample lies in the path of the strip-shaped X-ray beam so that a slice of the sample is irradiated by the strip-shaped X-ray beam. The substrate and the sample are rotated with respect to the initial position around a rotation axis over a predetermined rotation angle during a time interval. The rotation axis is perpendicular to the substrate. During the time interval, the substrate and the sample are tilted with respect to the initial position around a tilting axis perpendicular to the rotation axis. The tilting is over a tilting angle that the rotation axis forms with the plane through which the central part of the strip-shaped X-ray beam extends, and the tilting angle varies between a first predetermined value and a second predetermined value. The X-ray radiation transmitted through and diffracted by the sample is detected during the time interval and analyzed.

An apparatus for performing the method of transmission mode X-ray diffraction analysis described above comprises a source of X-ray radiation that generates X-ray radiation having a strip-shaped X-ray beam with a central part that extends along a plane. A substrate transparent to X-ray radiation is adapted for receiving a sample. The apparatus comprises means for rotating the substrate around a rotation axis over a predetermined rotation angle. The rotation axis is perpendicular to the substrate. The apparatus comprises means for tilting the substrate over a tilting angle around a tilting axis that is perpendicular to the rotation axis. Electromechanical means are used for rotating and tilting the substrate. A detector detects the X-ray radiation that is transmitted through and diffracted by the sample.

A second method of transmission mode X-ray diffraction analysis comprises the following steps. A plurality of samples to be analyzed are placed on a corresponding plurality of substrates of a sample holder. Each of the plurality of substrates is transparent to X-ray radiation. X-ray radiation is generated by means of an X-ray radiation source that generates a strip-shaped X-ray beam with a central part that extends along a path in a plane. The sample holder is placed in an apparatus comprising means for moving and positioning the sample holder so that a pre-selected sample can be positioned in the path of the strip-shaped X-ray beam. The pre-selected sample and a corresponding pre-selected substrate are placed in an initial position in which the pre-selected sample lies in the path of the strip-shaped X-ray beam so that a slice of the pre-selected sample is irradiated by the strip-shaped X-ray beam. The pre-selected substrate and the pre-selected sample are rotated with respect to the initial position around a rotation axis over a predetermined rotation angle during a time interval. The rotation axis is perpendicular to the substrate. During the time interval, the pre-selected substrate and the pre-selected sample are tilted with respect to the initial position around a tilting axis. The tilting axis is perpendicular to the rotation axis. The tilting is over a tilting angle that the rotation axis forms with the plane through which the central part of the strip-shaped X-ray beam extends, and the tilting angle varies between a first predetermined value and a second predetermined value. The X-ray radiation transmitted through and diffracted by the pre-selected sample during the time interval is detected and analyzed.

An apparatus for performing a second method of transmission mode X-ray diffraction analysis comprises a source of X-ray radiation that generates X-ray radiation having a strip-shaped X-ray beam with a central part that extends along a plane. A sample holder comprises a plurality of substrates transparent to X-ray radiation. Each substrate is adapted for receiving a sample to be analyzed. The apparatus comprises means for positioning a preselected substrate and thereby a sample on it in an initial position at which the sample lies in the path of the strip-shaped X-ray beam. The apparatus further comprises means for rotating the preselected substrate and thereby the sample on it around a rotation axis over a predetermined rotation angle. The rotation axis is perpendicular to the substrate. The apparatus further comprises means for tilting the preselected substrate and thereby the sample on it over a tilting angle around a tilting axis that is perpendicular to the rotation axis. Electro-mechanical means are used for rotating and tilting the plurality of substrates. A detector is used to detect the X-ray radiation that is transmitted through and diffracted by each sample.

The methods and apparatuses are used to perform X-ray transmission diffraction analysis with significantly improved particle statistics. Particle statistics is a term known in the art. "Improved particle statistics" is defined as obtaining a powder diffraction pattern with more reliable diffracted beam intensities, or diffracted beam intensities with reduced standard deviation.

Additionally, the methods and apparatuses are used to perform X-ray transmission diffraction analysis of a plurality of samples in a time effective way.

BRIEF DESCRIPTION OF THE DRAWINGS

A description of embodiments is set forth below with reference to the accompanying drawings. These embodiments are set forth to aid the understanding of the invention, but are not to be construed as limiting.

FIG. 16 shows a cross-sectional view of an embodiment of a sample container 11 wherein a foil 19 is the bottom wall of the sample container.

Figure 1:
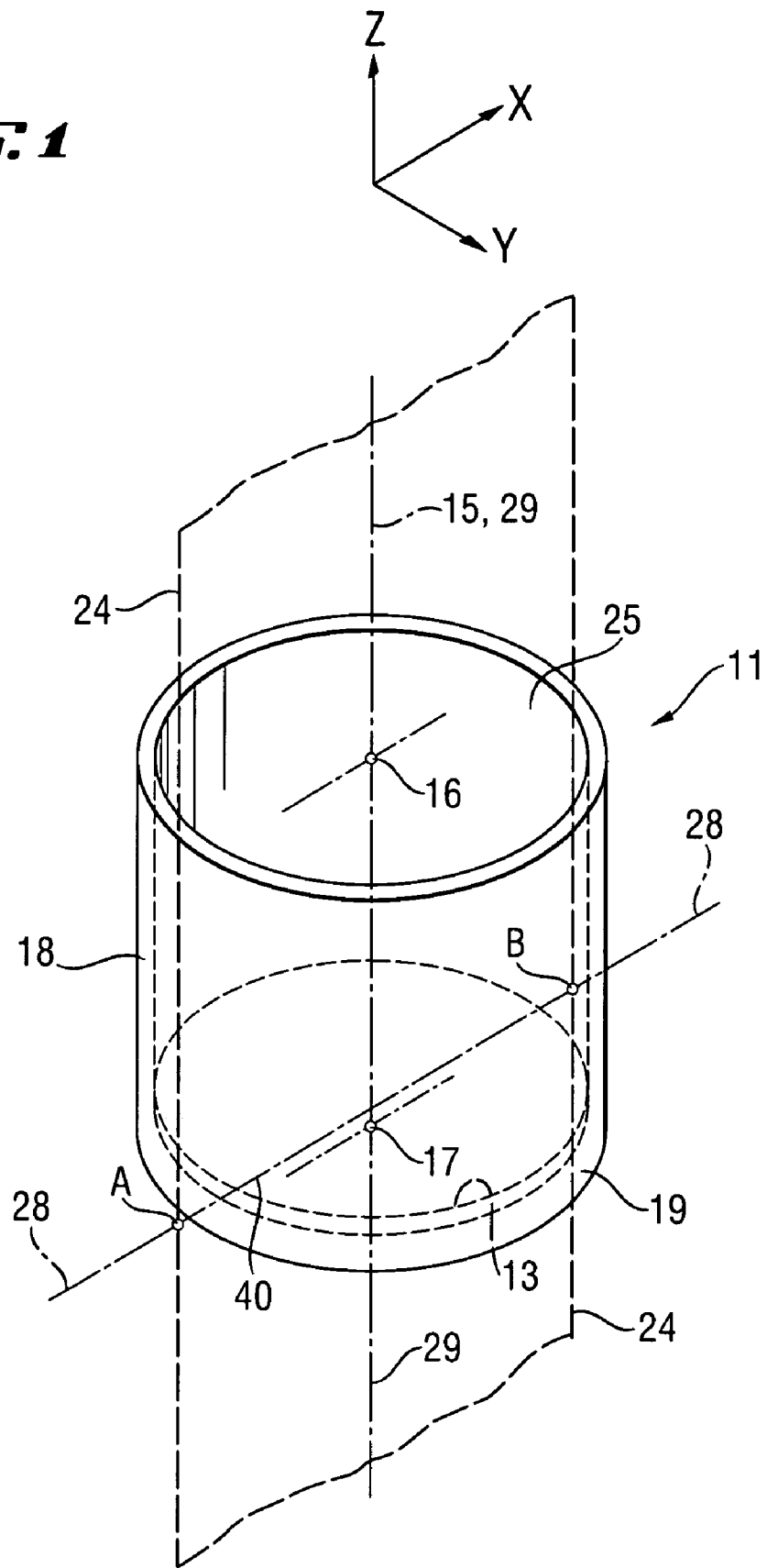
FIG. 1 shows a sample container 11 of multiple-sample holder 12 shown by FIG. 10 and a strip-shaped X-ray beam 24 which irradiates a sample placed on a substrate 19.

REFERENCE NUMERALS IN DRAWINGS 11 sample container/single well/a well of a multiple-well tray
12 multiple-sample holder/multiple-well tray
13 sample volume/sample layer
14 inner surface of the bottom wall 19 of sample container 11
15 symmetry axis of sample container 11
16 center of upper opening of sample container 11
17 center of planar substrate or substrate 19 /center of the bottom wall 19
18 side wall of sample container 11
19 substrate/bottom wall of sample container 11/foil
20 primary X-ray beam
21 X-ray source
22 detector
23 monochromator for focusing X-ray beam onto a line segment
24 strip shaped X-ray beam directed onto sample
25 chamber
26 diffracted X-ray beam
27 slice of the sample/slice of volume 13 irradiated by beam 24
28 tilting axis
29 rotation axis
30 detector circle
31 table for rotating and tilting multiple-sample holder 12
40 line segment
41 X-ray tube
42 shutter
43 Soller slit
44 curved monochromator
45 slit
46 slit
47 sample holding substrate
48 diffracted beam
49 Beryllium window
51 anode wire
52 delay line
53 position sensitive detector
61 mounting plate
62 edge of mounting plate
63 edge of mounting plate 71 support frame
72 guide rail
73 guide rail
81 support frame
82 support
83 support
84 motor
85 mechanical transmission element
86 mechanical transmission element
θ Bragg angle
T tilting angle

DETAILED DESCRIPTION OF EMBODIMENTS

In the following description the term "sample" is used to designate a sample comprising one or more crystals as well as a powder sample. A "powder sample" is defined herein as a powder sample of a compound of which the diffraction or crystallization behavior is to be determined. Such a compound may be a chemical substance, or a mixture of different substances. A compound may comprise an organic or organometallic molecular compound, such as a pharmaceutically active molecule or catalyst-ligand complex or a dimer, salt, ester, solvate or functional part thereof. A powder sample of the present invention may also comprise a biomolecule, for instance a nucleic acid (such as DNA, RNA and PNA), a polypeptide, peptides, glycoprotein and other proteinaceous substances, a lipoprotein, protein-nucleic acid complex, carbohydrate, biomimetic or a functional part, derivative and/or analogue thereof.

It is to be noted that the powder sample may indeed be in the form of a powder. A "powder sample" also includes a number of crystals which are contained in a solid material, such as is the case for metals, polymers, etc. Thus, in the latter case, the powder sample appears as a solid material in one piece. Moreover, powder samples may comprise only a limited number of crystals.

EXAMPLE 1

First Embodiment of a Method of Transmission Mode X-ray Diffraction Analysis A first embodiment of a method of transmission mode X-ray diffraction analysis of a single sample is described hereinafter with reference to FIGS. 1-5.

Figure 10:
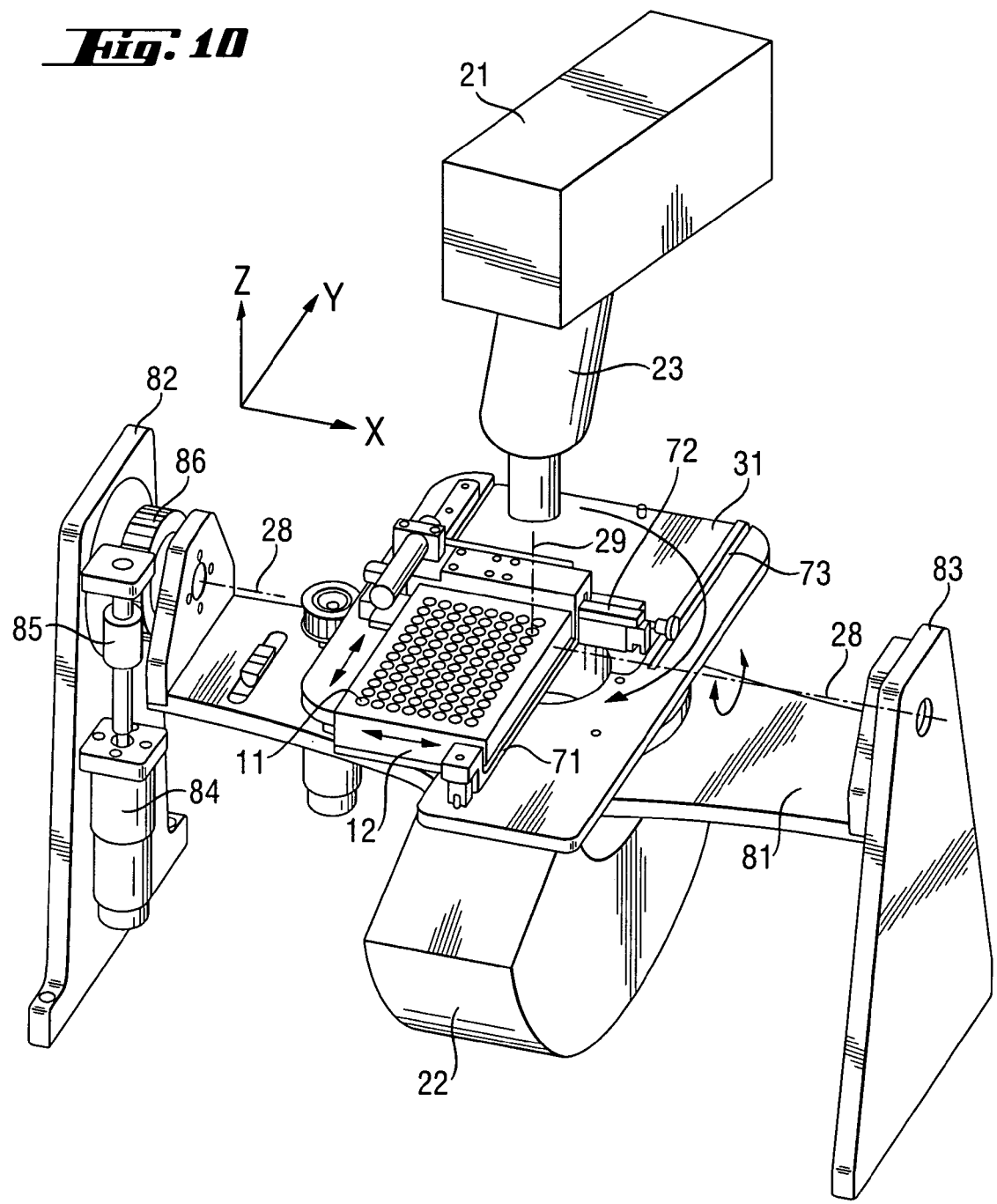
FIG. 10 shows an apparatus for performing transmission mode X-ray diffraction analysis of a plurality of samples.

FIG. 1 shows a sample container 11, which is, for example, a single well or one of the wells of a multiple-well tray 12 shown by FIG. 10, and of a strip-shaped X-ray beam 24 which irradiates a sample placed on a substrate 19, which is, for example, the bottom wall of sample container 11. The term "strip-shaped X-ray beam" means that the beam extends along a planar, strip-shaped irradiation region and that the beam has a cross section which is approximately rectangular. Coordinate axis X, Y, Z which are normal to each other are shown in FIG. 1 for reference.

The region irradiated by the X-ray beam is the volume over which the X-ray beam extends. If the X-ray beam has approximately the shape of a flat strip, then the shape of the irradiated region is strip-shaped. In that case, the irradiated region has, for example, approximately the shape of a right rectangular prism, the length of the prism being much larger than its width and the width of the prism being much larger than its thickness.

The term "strip-shaped irradiation region" thus means that the length of the irradiated region is much larger than its width and that the width of the irradiated region is much larger than the thickness thereof.

In the attached drawings, and in particular in FIGS. 1, 2, 4 and 5, strip-shaped X-ray beam 24 is schematically represented as a plane, but in fact only the central part of the beam extends along a plane.

Figure 2:
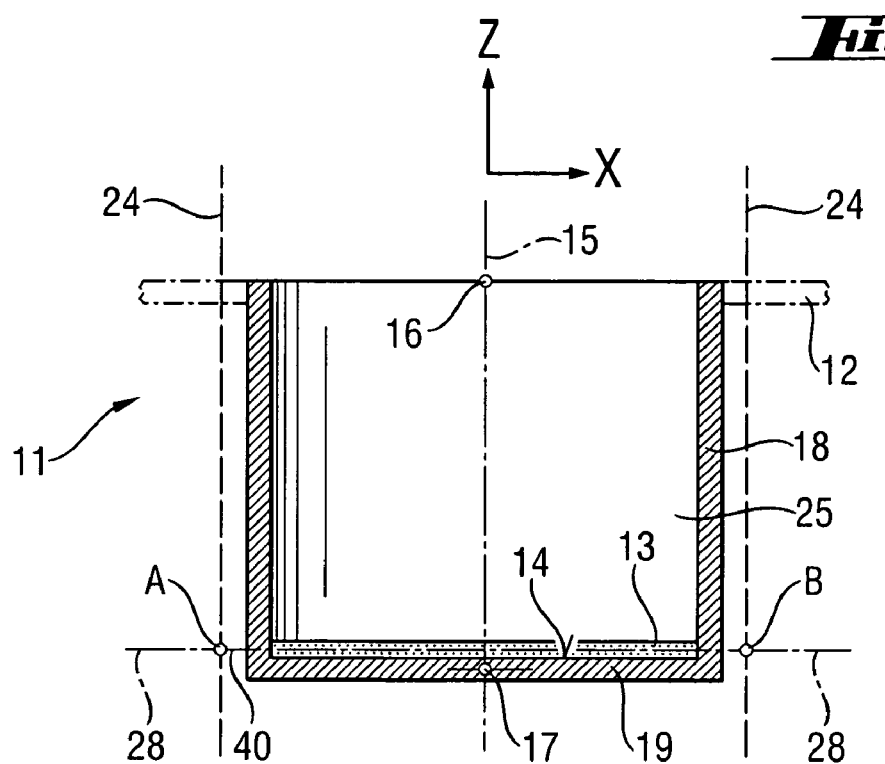
FIG. 2 shows a cross-sectional view of a sample container 11 along the plane which passes through symmetry axis 15 (shown in FIG. 1) of sample container 11 and in which X-ray beam 24 extends.

FIG. 2 shows a cross-sectional view of sample container 11 of FIG. 1 along the plane parallel to the X-Z plane and which passes through symmetry axis 15 (shown in FIG. 1) of sample container 11, and which is the plane in which X-ray beam 24 extends. As shown by FIG. 2, sample container 11 defines a chamber 25 which extends between the bottom wall 19 and the upper end of sample container 11. Chamber 25 is, for example, cylindrical and has, for example, a circular cross section.

Figure 3:
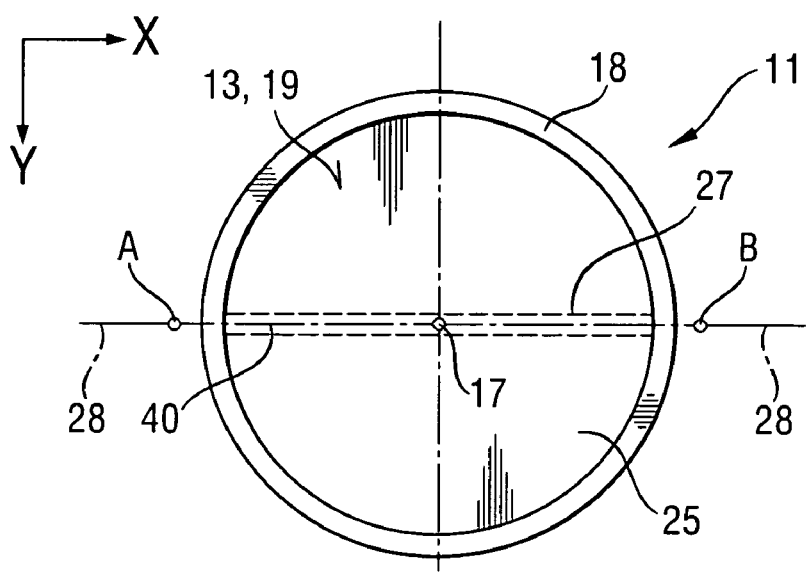
FIG. 3 shows a top view of sample container 11.

FIG. 3 shows a top view of sample container 11 in FIG. 1.

Figure 4:
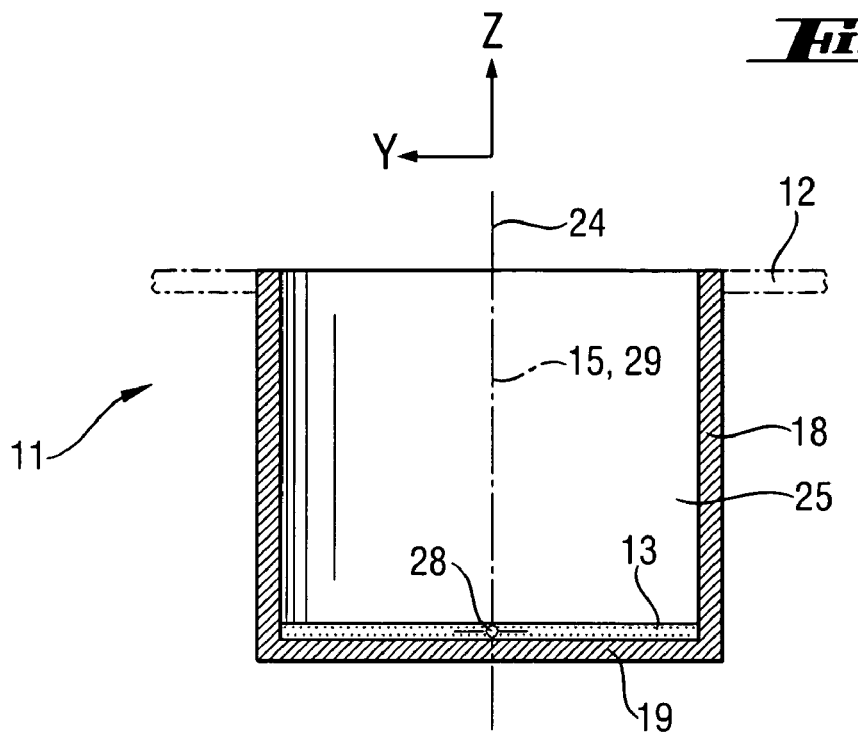
FIG. 4 shows a cross-sectional view of a sample container 11 along the plane which passes through symmetry axis 15 and is perpendicular to the plane in which X-ray beam 24 extends. In this view, sample container 11 is at an initial position with a tilting angle equal to zero.

FIG. 4 shows a cross-sectional view of sample container 11 of FIG. 1 taken along the plane parallel to the Y-Z plane and which passes through symmetry axis 15 and which is perpendicular to the plane in which X-ray beam 24 extends. In this view, sample container 11 is at an initial position with a tilting angle equal to zero.

Figure 5:
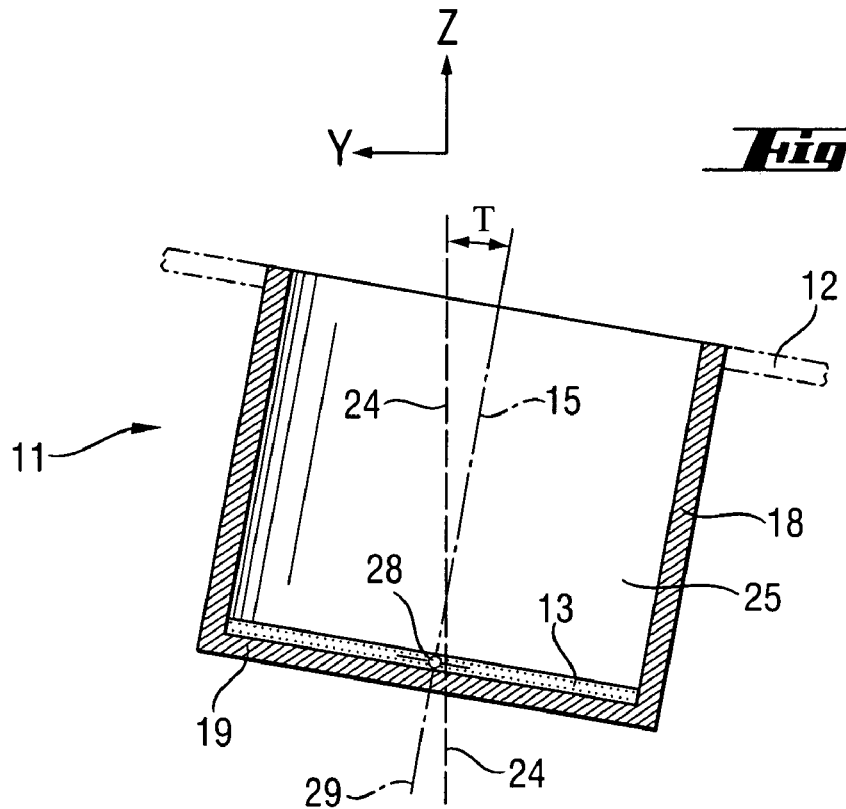
FIG. 5 shows a cross-sectional view of sample container 11 shown in FIGS. 1 to 4, but in this view, sample container 11 is in a tilted position with a tilting angle T between the symmetry axis 15 of sample container 11 and the plane in which X-ray beam 24 extends.

FIG. 5 shows a cross-sectional view of sample container 11 similar to the view shown in FIG. 4, but in this view, sample container 11 is in a tilted position with a tilting angle T between the symmetry axis 15 of sample container 11 and the plane in which X-ray beam 24 extends.

One embodiment of a method of transmission mode X-ray diffraction analysis comprises the following steps:
(A) a sample to be analyzed is placed on substrate 19 which is adapted for receiving and holding a sample and which is transparent to X-ray radiation,
(B) a strip-shaped X-ray beam 24 is generated by means of an X-ray radiation source 21 (not shown in FIGS. 1 to 5). As shown by FIGS. 1, 2, 4 and 5, the central part of beam 24 extends along a plane,
(C) the substrate 19 and thereby the sample placed thereon are positioned by suitable electromechanical means in the initial position shown by FIG. 4 in which that sample lies in the path of X-ray beam 24. When substrate 19 is in that initial position a slice 27 (shown by FIG. 3) of a volume element 13, which contains the sample, and thereby a slice of the sample itself is irradiated by beam 24,
(D) the following movements of substrate 19 with respect to the initial position thereof are effected:
(i) a rotation of substrate 19 and thereby of the sample around a rotation axis 29, and
(ii) a tilting of substrate 19 and thereby of the sample around a tilting axis 28 and over a tilting angle T that varies between a first and a second predetermined value, and
(E) X-ray radiation transmitted through and diffracted by the sample is detected during a time interval during which the above-mentioned movements of the substrate 19 are effected.

The method discussed above irradiates a sample slice with the X-ray beam so that more crystals contribute to diffraction. This improves the particle statistics if compared to a method wherein the sample is irradiated with an X-ray beam focused on a point. Moreover, by irradiating a sample slice with the X-ray beam the irradiated area is larger than when a point focused beam is used, and this reduces the measuring time because a time-consuming scanning of the sample with a point focused beam is not required.

Substrate 19 may be a wall or a foil made, for example, of an X-ray transparent plastic material, for example, Kapton® (Du Pont) or Mylar® (Du Pont). Substrate 19 may be a plane or planar wall.

Substrate 19 may also be optically transparent, i.e. transparent to visible radiation.

Substrate 19 is, for example, the bottom wall 19 of sample container, for example, of a sample container 11, which has, for example, a cylindrical side wall 18 and which has an upper opening. Substrate 19 has an inner surface 14. The sample to be analyzed is placed on this surface of substrate 19.

The sample to be analyzed is placed in a volume element 13 which as shown in FIG. 1 is, for example, a thin layer located at the bottom of sample container 11 and on substrate 19. Volume element 13 is designated hereinafter also as sample layer 13. The sample can but must not necessarily occupy a substantial part of or the entire volume of volume element 13.

The strip-shaped X-ray beam 24 illuminates a line segment 40 which is oriented in the direction of the tilting axis 28. Line segment 40 preferably coincides with the tilting axis 28 and extends between points A and B shown in FIGS. 1, 2 and 3. In an embodiment the length of line segment 40 is adjusted to be equal to or approximately equal to the inner diameter of the sample container.

As shown by FIGS. 1, 2 and 3, line segment 40 lies at the intersection of X-ray beam 24 with the plane which contains tilting axis 28. As shown by FIG. 3, the latter plane passes through the center of sample layer 13.

As shown by FIG. 1, sample container 11 has a symmetry axis 15 which is perpendicular to substrate 19 and which passes through the center 17 of substrate 19 and through the center 16 of the upper opening of sample container 11.

As shown by FIGS. 1 and 4, in an embodiment, the central axis of beam 24 coincides with the symmetry axis 15 and with rotation axis 29 of sample container 11 when the tilting angle is zero.

As shown by FIG. 5, the tilting angle T is the angle that rotation axis 29 forms with the plane through which the central part of beam 24 extends.

As shown by FIGS. 1-5, tilting axis 28 lies in the plane through which the central part of beam 24 extends and is perpendicular to rotation axis 29. As shown by FIGS. 2, 4 and 5, tilting axis 28 passes through the center of sample layer 13.

In one embodiment, the tilting of substrate 19 covers a tilting angle T between zero degrees, as defined by the initial position of substrate 19, and a predetermined value greater than zero, for example, 10 degrees.

In a second embodiment, the rotation and tilting movements of substrate 19 are performed simultaneously and continuously. In a third embodiment, the tilting movement of substrate 19 is performed stepwise, and a rotation thereof covering a predetermined rotation angle is performed for each tilting step.

In a fourth embodiment, the central axis of beam 24 coincides with the symmetry axis 15 and with rotation axis 29 of sample container 11 when the tilting angle is zero.

In a fifth embodiment, the central axis of beam 24 and rotation axis 29 pass through the center 17 of substrate 19 when the substrate 19 is in the initial position.

In a sixth embodiment, the radiation source 21 and thereby beam 24 are stationary, and substrate 19 is moved with respect to beam 24.

In a seventh embodiment, the rotation of substrate 19 covers an angle which is equal to or close to 360 degrees. In an eighth embodiment, the rotation of substrate 19 covers an angle which is less than 360 degrees. In a ninth embodiment, the rotation of substrate 19 covers an angle which is greater than 360 degrees.

EXAMPLE 2

Figure 6:
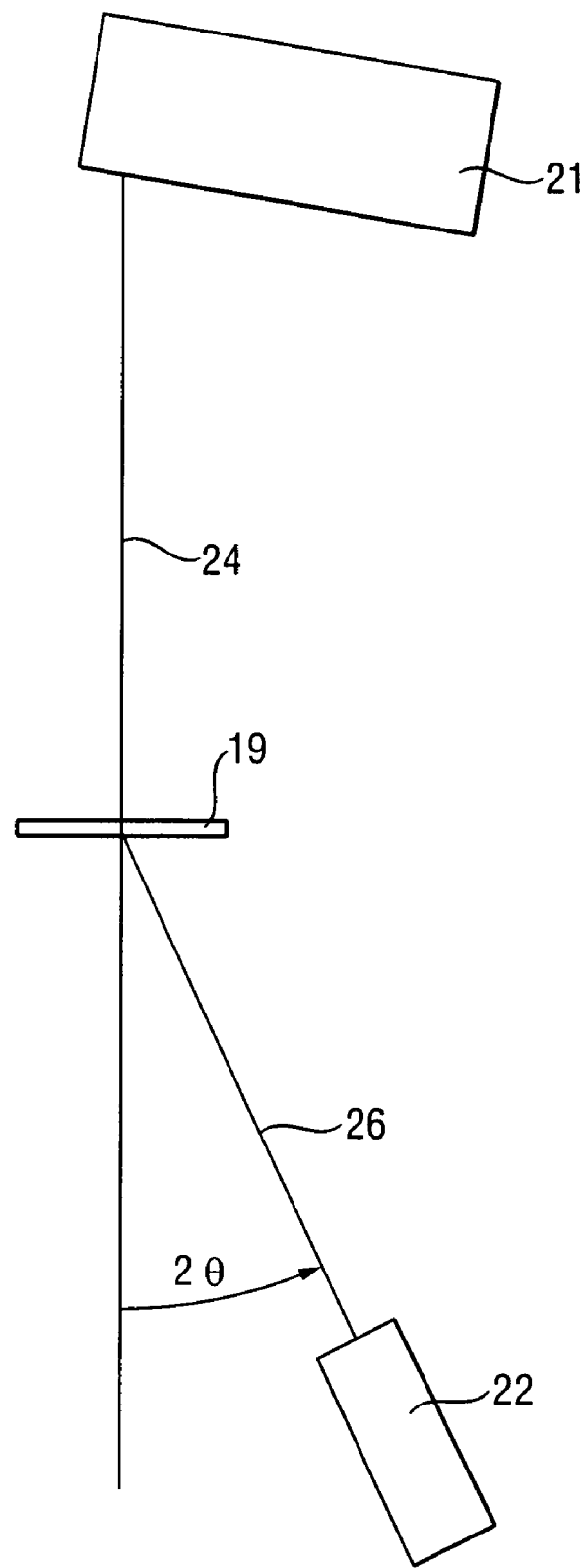
FIG. 6 shows a cross-sectional view of the structure of a first embodiment of an apparatus for carrying out a method of transmission mode X-ray diffraction analysis.

First Embodiment of an Apparatus Used to Conduct Transmission Mode X-ray Diffraction Analysis FIG. 6 shows a cross-sectional view of the structure of a first embodiment of an apparatus used to conduct transmission mode X-ray diffraction analysis. The cross-section shown by FIG. 6 is taken along a plane parallel to the plane Y-Z in FIG. 1 and passing through the center of substrate 19. The apparatus shown by FIG. 6 comprises an X-ray radiation source 21 that provides X-ray beam 24 for irradiating a sample placed on a substrate 19, and a detector 22 for detecting X-ray radiation 26 transmitted through and diffracted by the sample. FIG. 6 shows the diffraction angle 2θ. θ is the Bragg angle.

The apparatus represented in FIG. 6 is a diffractometer and comprises an X-ray radiation source 21 which is adapted to provide a strip-shaped X-ray beam 24 the central part of which extends along a plane as shown in FIGS. 1, 2, 4 and 5.

The apparatus represented in FIG. 6 further comprises electromechanical means (not shown in FIG. 6) for:

(A) positioning substrate 19 and thereby the sample in an initial position in which the sample lies in the path of beam 24 and a slice 27 (shown by FIG. 3) of a volume element 13, which contains the sample, and thereby a slice of the sample itself is irradiated by beam 24, (B) effecting the following movements of the substrate 19 with respect to the initial position:

(i) a rotation of substrate 19 and thereby of the sample around a rotation axis 29 which is perpendicular to the substrate, the rotation covering a predetermined rotation angle, and (ii) a tilting of substrate 19 and thereby of the sample around a tilting axis 28 which lies in the plane through which the central part of beam 24 extends and which is perpendicular to rotation axis 29, the tilting covering a tilting angle T that varies between a tilting angle of zero, defined by the initial position of substrate 19, and a predetermined value greater than zero, for example, 10 degrees.

The apparatus represented in FIG. 6 further comprises a detector 22 for detecting X-ray radiation transmitted through and diffracted by the sample during a time interval over which the above-mentioned movements of the substrate 19 are effected.

As already described with reference to FIGS. 1-4, in the embodiment shown by FIG. 6, strip-shaped X-ray beam 24 illuminates a line segment 40 which is oriented in the direction of tilting axis 28. Line segment 40 preferably coincides with tilting axis 28 and extends between points A and B shown in FIGS. 1, 2 and 3.

In an embodiment, the length of line segment 40 is adjusted to be equal to or approximately equal to the inner diameter of the sample container.

Substrate 19 is, for example, as described above with reference to FIGS. 1 to 5. Substrate 19 is, for example, the bottom wall 19 of sample container, for example, of a sample container 11, which has, for example, a cylindrical side wall 18 and which has an upper opening.

FIG. 16 shows a cross-sectional view of an embodiment of a sample container 11 wherein a foil 19 is the bottom wall of the sample container. The cross-section shown by FIG. 16 is taken along a plane parallel to the plane X-Z in FIG. 1 and passing through the center of substrate 19.

As shown in the embodiment of sample container 11 represented in FIG. 16, the bottom wall of sample container 11, and therefore the substrate on which sample layer 13 is deposited, is a foil 19, for example, a Kapton® foil, which closes the lower opening of a container 11 of the type shown in FIGS. 1-5 and which is transparent to X-ray radiation. In the embodiment shown in FIG. 16, a mounting plate 61 is used to fix foil 19 on the lower end of sample container 11. For this purpose, sample container 11, foil 19 and mounting plate 61 are assembled together as shown by FIG. 16. Mounting plate 61 has, for example a circular opening which is aligned with the cross-section of chamber 25 of sample container 11 and thereby allows passage of a beam diffracted by a sample deposited on foil 19 in chamber 25. As shown by FIG. 16, the circular opening has edges 62, 63, each of which forms an angle of, for example, about 45 degrees with the plane where foil 19 lies. The shape of the edges 62, 63 allows an enhancement of the region through which the diffracted beam passes.

When substrate 19 is in the initial position, the central axis of beam 24 and rotation axis 29 pass through the center 17 of substrate 19.

In an embodiment, detector 22 is a movable detector. In another embodiment, detector 22 is a stationary detector which lies in a portion of a spherical surface.

In a further embodiment of the apparatus, the means for moving sample substrate 19 are adapted for effecting a rotation of substrate 19 covering an angle which is equal to or close to 360 degrees. In another embodiment, the rotation of substrate 19 covers an angle which is less than 360 degrees. In yet another embodiment, the rotation of substrate 19 covers an angle which is greater than 360 degrees.

EXAMPLE 3

Figure 7:
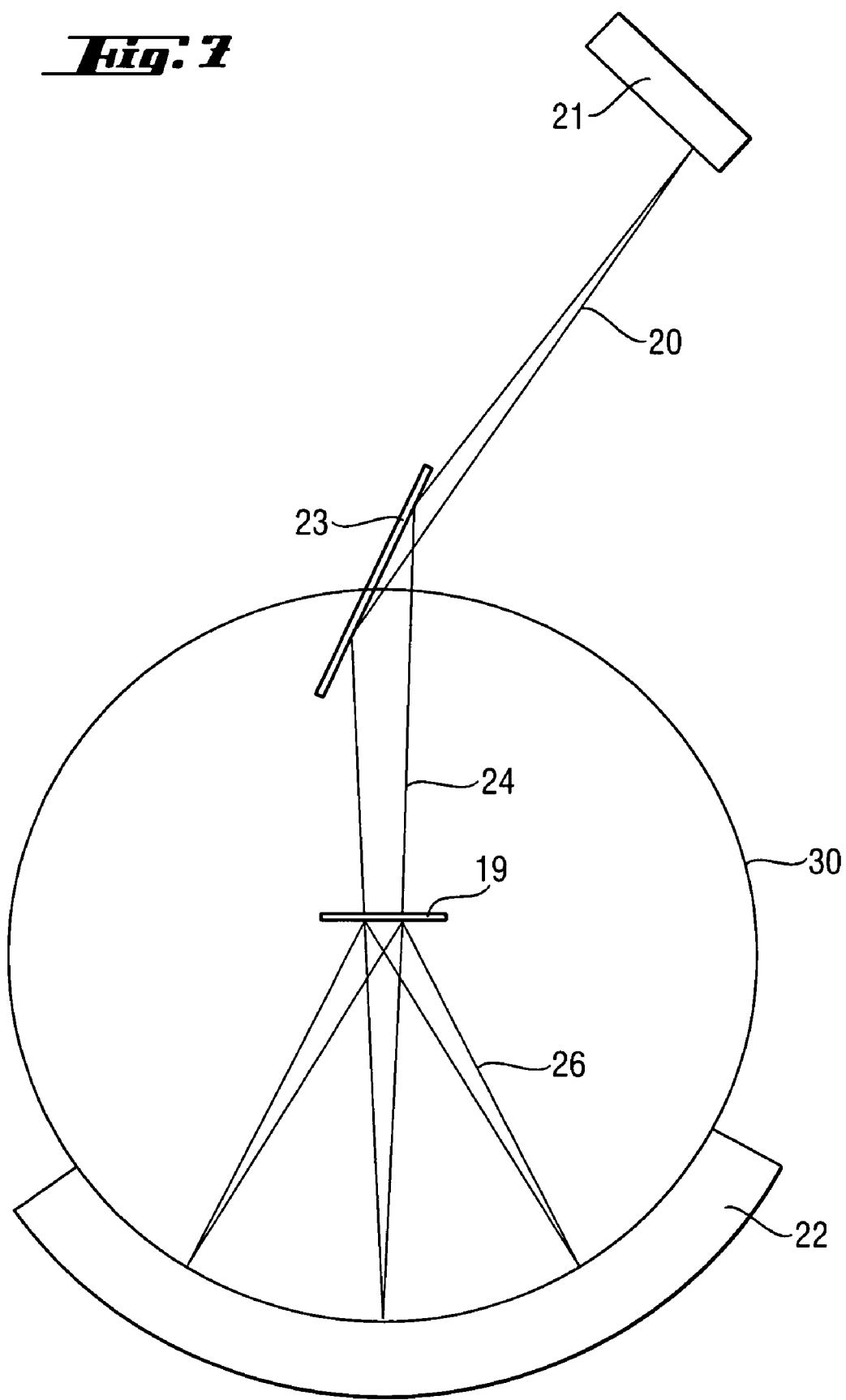
FIG. 7 shows a cross-sectional view of the structure of a second embodiment of an apparatus for carrying out a method of transmission mode X-ray diffraction analysis.

Second Embodiment of an Apparatus Used to Conduct Transmission Mode X-ray Diffraction FIG. 7 shows a cross-sectional view of the structure of a second embodiment of an apparatus used to conduct transmission mode X-ray diffraction analysis. The cross-section shown by FIG. 7 is taken along a plane parallel to the plane Y-Z in FIG. 1 and passing through the center of substrate 19. The apparatus shown by FIG. 7 is a diffractometer and generally comprises the components of the apparatus described above with reference to FIG. 6 and in addition comprises means for focusing X-ray beam 24, for example, a Germanium (111) monochromator 23 that is located in the path of beam 24 and between X-ray source 21 and substrate 19 which holds the sample to be analyzed. In this embodiment, detector 22 is a stationary detector which lies in a portion of a spherical surface 30.

EXAMPLE 4

Figure 8:
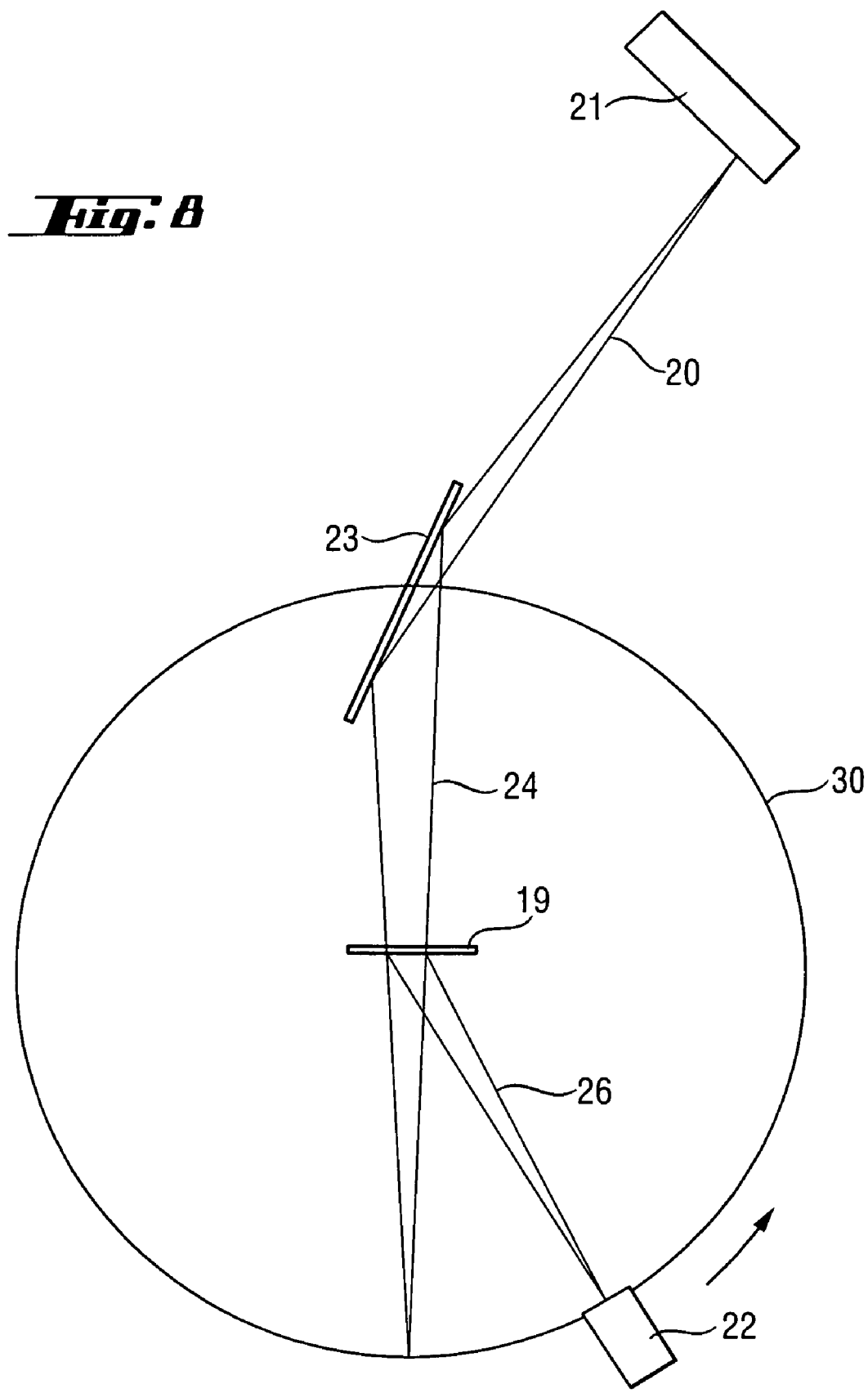
FIG. 8 shows a cross-sectional view of the structure of a third embodiment of an apparatus for carrying out a method of transmission mode X-ray diffraction analysis.

Third Embodiment of an Apparatus Used to Conduct Transmission Mode X-ray Diffraction Analysis FIG. 8 shows a cross-sectional view of the structure of a third embodiment of an apparatus used to conduct transmission mode X-ray diffraction analysis. The cross-section shown by FIG. 8 is taken along a plane parallel to the plane Y-Z in FIG. 1 and passing through the center of substrate 19. The apparatus shown by FIG. 8 generally comprises the components of the diffractometer described above with reference to FIG. 7 with the exception that in the embodiment shown by FIG. 8, the detector comprises at least one movable detector 22.

EXAMPLE 5

Figure 9:
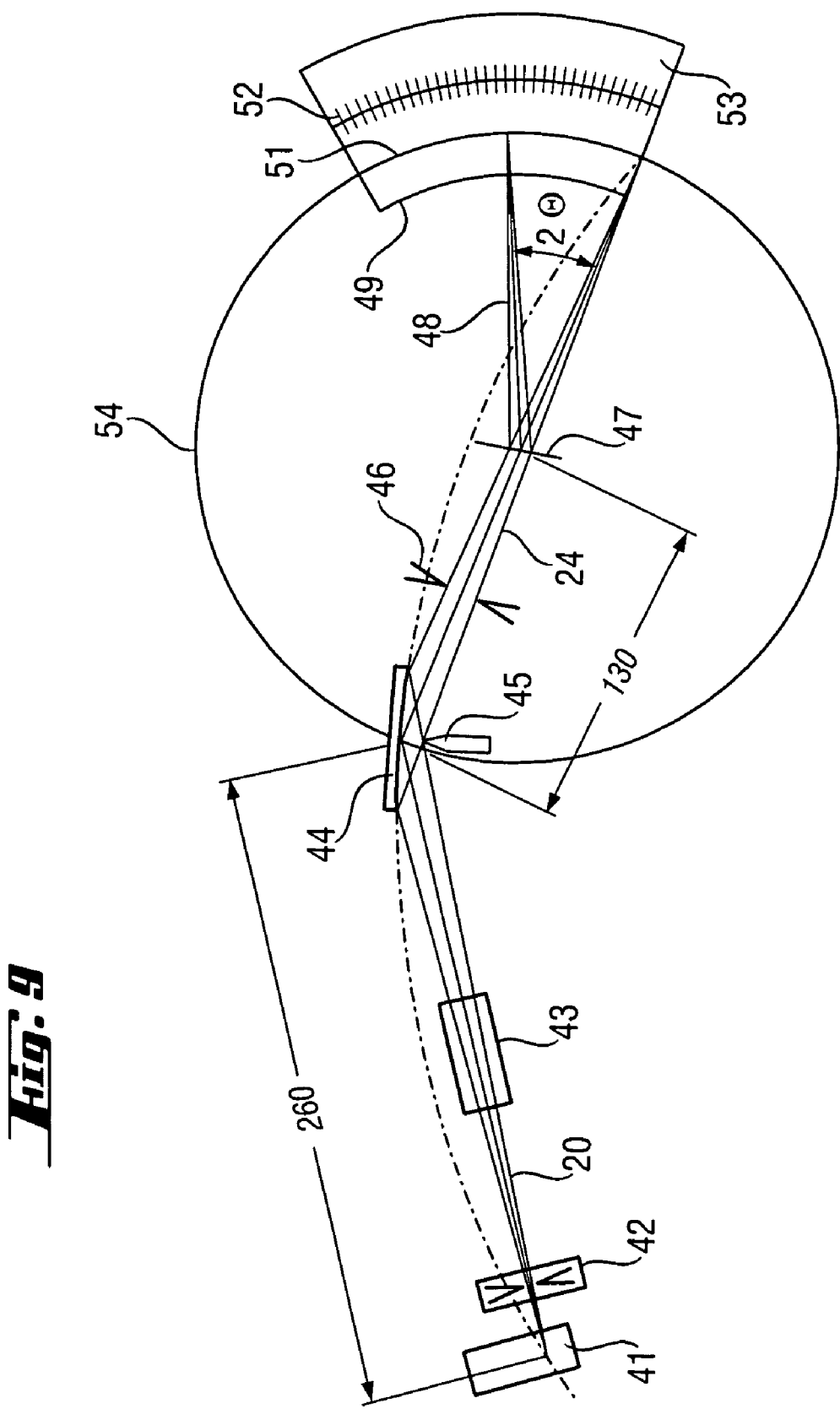
FIG. 9 shows a cross-sectional view of the structure of a fourth embodiment of an apparatus for carrying out a method of transmission mode X-ray diffraction analysis.

Fourth Embodiment of an Apparatus Used to Conduct Transmission Mode X-ray Diffraction Analysis FIG. 9 shows a cross-sectional view of the structure of a fourth embodiment of an apparatus used to conduct transmission mode X-ray diffraction analysis. The cross-section shown by FIG. 9 is taken along a plane parallel to the plane Y-Z in FIG. 1 and passing through the center of substrate 19. The apparatus shown by FIG. 9 has generally the structure of the apparatus described above with reference to FIG. 7.

A diffractometer according to this fourth embodiment comprises the following components arranged as shown in FIG. 9:
an X-ray tube 41,
a curved Germanium (111) monocromator 44 mounted on the circumference 54 of the diffractometer,
a position sensitive detector 53,
a shutter 42,
a Soller slit 43,
slits 45 and 46,
a substrate 47 that holds a sample, and
a Beryllium window 49.

Monocromator 44 receives a primary X-ray beam 20 provided by X-ray tube 41 and supplies a convergent monochromatic $K\alpha_1$ X-ray beam 24 which is focused in 2θ (2 Theta) at the point O. With the arrangement shown in FIG. 9, diffracted beams 48 diffracted by a sample placed on substrate 47 are focused on a circle 54 of radius r=130 millimeter within a range 2θ of about 40 degrees. This is useful for a stationary curved position sensitive detector (PSD) 53. Detector 53 comprises a delay line 52. The anode wire 51 of position sensitive detector 53 lies on a circle segment that coincides with a segment of the focusing circle 54, and the diffracted beams 48 always enter perpendicular to the counter surface, in contrast to conventional Guinier or Seemann-Bohlin techniques.

The apparatus shown by FIG. 9 comprises electromechanical means for positioning and moving substrate 47. The latter means are as described for the embodiment described with reference to FIG. 6.

EXAMPLE 6

Second Embodiment of a Method of Transmission Mode X-ray Diffraction Analysis

A second embodiment of a method of transmission mode X-ray diffraction analysis is described hereinafter with reference to FIGS. 1-5 and 10. This method serves for transmission mode X-ray diffraction analysis of a plurality of samples by means of an apparatus comprising an X-ray radiation source 21 and a detector 22 for detecting X-ray radiation transmitted through and diffracted by the sample.

Strip shaped X-ray beam 24, sample layer 13, line segment 40 and tilting axis 28 are as described above with reference to FIGS. 1-5.

FIG. 10 shows a perspective view of an apparatus for performing this second embodiment of a method of transmission mode X-ray diffraction analysis.

The second embodiment of a method of transmission mode X-ray diffraction analysis comprises the following steps:

(A) a plurality of samples to be analyzed is placed on respective substrates 19 of a multiple-sample holder 12. Each substrate 19 is adapted for receiving and holding a sample and is transparent to X-ray radiation, (B) a strip-shaped X-ray beam 24 is generated by means of an X-ray radiation source 21 (shown in FIG. 10). As shown by FIGS. 1, 2, 4 and 5, the central part of beam 24 extends along a plane, (C) a multiple-sample holder 12 is placed in an apparatus comprising means for moving and positioning multiple-sample holder 12 so that a pre-selected substrate 19 can be positioned in the path of beam 24. When the pre-selected substrate 19 is in the initial position a slice 27 (shown by FIG. 3) of a volume element 13, which contains the sample, and thereby a slice of the sample itself is irradiated by beam 24, (D) a pre-selected substrate 19 of the multiple-sample holder 12 is positioned in the initial position in which the sample lies in the path of the beam 24 and a slice 27 of the sample is irradiated by the beam 24, (E) the following movements of the pre-selected substrate 19 with respect to the initial position are effected:
  (i) a rotation of the pre-selected substrate 19 and thereby of the sample around a rotation axis 29, and
  (ii) a tilting of the pre-selected substrate 19 and thereby of the sample around a tilting axis 28 and over a tilting angle T that varies between a first and a second predetermined value, and (F) X-ray radiation that is transmitted through and diffracted by the sample is detected during a time interval during which the above-mentioned movements of the pre-selected substrate 19 are effected.

The positioning of the pre-selected substrate 19 described above under (D) is effected by suitable translation and/or rotation movements of multiple-sample holder 12 that bring the substrate to the initial position.

The movements described above under (E1) and (E2) are effected by corresponding movements of multiple-sample holder 12.

Substrate 19 may be a wall or a foil made, for example, of an X-ray transparent plastic material, e.g. Kapton® (Du Pont) or Mylar® (Du Pont). Substrate 19 may be a plane or planar wall. Substrate 19 may also be optically transparent, i.e. transparent to visible radiation.

As shown by FIGS. 2, 4 and 5 substrate 19 is, for example, the bottom wall of sample container, for example, of a sample container 11, which has, for example, a cylindrical side wall 18 and which has an upper opening.

The sample to be analyzed is placed in a volume element 13 which as shown in FIG. 1 is, for example, a thin layer located at the bottom of sample container 11 and on substrate 19. Volume element 13 is designated hereinafter also as sample layer 13. The sample can but must not necessarily occupy the entire volume of volume element 13.

As shown by FIG. 1, sample container 11 has a symmetry axis 15 which is perpendicular to substrate 19 and which passes through the center 17 of substrate 19 and through the center 16 of the upper opening of sample container 11.

As shown by FIGS. 1, 4 and 5, in an embodiment, the rotation axis 29 coincides with the symmetry axis 15 of sample container 11.

As shown by FIG. 5, the tilting angle T is the angle that rotation axis 29 forms with the plane through which the central part of beam 24 extends.

As shown by FIGS. 1-5, tilting axis 28 lies in the plane through which the central part of beam 24 extends and is perpendicular to rotation axis 29. As shown by FIGS. 2, 4 and 5, tilting axis 28 passes through the center of sample layer 13.

In one embodiment, the tilting of substrate 19 covers a tilting angle T between zero degrees, as defined by the initial position of substrate 19, and a predetermined value greater than zero, for example, 10 degrees.

In a second embodiment, the rotation and tilting movements of substrate 19 are performed simultaneously and continuously. In a third embodiment, the tilting movement of substrate 19 is performed stepwise, and a rotation thereof covering a predetermined rotation angle is performed for each tilting step.

In a fourth embodiment, the rotation axis 29 coincides with the symmetry axis 15 of sample container 11.

In a fifth embodiment, the central axis of beam 24 and rotation axis 29 pass through the center 17 of substrate 19 when the substrate 19 is in the initial position.

In a sixth embodiment, the radiation source 21 and thereby beam 24 are stationary, and substrate 19 is moved with respect to beam 24.

In a seventh embodiment, the rotation of substrate 19 covers an angle which is equal to or close to 360 degrees. In an eighth embodiment, the rotation of substrate 19 covers an angle which is less than 360 degrees. In a ninth embodiment, the rotation of substrate 19 covers an angle which is greater than 360 degrees.

EXAMPLE 7

Fifth Embodiment of an Apparatus Used to Conduct Transmission Mode X-ray Diffraction Analysis FIG. 10 shows an apparatus used to conduct transmission mode X-ray diffraction analysis of a plurality of samples. This apparatus comprises an X-ray radiation source 21 that provides X-ray beam 24 for irradiating a sample, and a detector 22 for detecting X-ray radiation 26 transmitted through and diffracted by the sample.

The apparatus shown by FIG. 10 comprises:
(A) an X-ray radiation source 21 which is adapted to provide a strip-shaped X-ray beam 24 the central part of which extends along a plane as shown in FIGS. 1, 2, 4 and 5,
(B) a multiple-sample holder 12 which comprises a plurality of substrates 19 each of which is adapted for receiving and holding a sample to be analyzed. Each of the substrates 19 is transparent to X-ray radiation,
(C) electromechanical-means for:
  (i) positioning a pre-selected substrate of multiple-sample holder 12 and thereby a sample in an initial position in which the sample lies in the path of beam 24 and a slice 27 (shown by FIG. 3) of a volume element 13, which contains the sample, and thereby a slice of the sample itself is irradiated by beam 24, and
  (ii) effecting the following movements of the pre-selected substrate 19 with respect to the above mentioned initial position thereof:
    (a) a rotation of the pre-selected substrate 19 and thereby of the sample around a rotation axis 29 which is perpendicular to the pre-selected substrate, the rotation covering a predetermined rotation angle, and
    (b) a tilting of the pre-selected substrate 19 and thereby of the sample around a tilting axis 28 which lies in the plane through which the central part of beam 24 extends and which is perpendicular to rotation axis 29, the tilting covering a tilting angle T that varies between a tilting angle of zero, defined by the initial position of substrate 19, and a predetermined value greater than zero, and (D) a detector 22 for detecting x-ray radiation transmitted through and diffracted by the sample during a time interval over which the above-mentioned movements of the substrate 19 are effected.

The above-mentioned electro-mechanical-means comprise, for example, a table 31 for rotating and tilting multiple-sample holder 12 for effecting the above-mentioned movements. As shown by FIG. 10, table 31 comprises a movable support frame 71 which is adapted for receiving and holding multiple-sample holder 12, a guide rail 72 oriented in X-direction, a guide rail 73 oriented in Y-direction, and motors for moving support frame 71 on table 31 along guide rails 72 and 73 respectively. The apparatus shown in FIG. 10 further comprises means for rotating table 31 about rotation axis 29 which is perpendicular to the table 31. These means include motor and mechanical transmission means which are not shown in detail in FIG. 10. The apparatus shown in FIG. 10 further comprises tilting means for tilting table 31 about tilting axis 28. These tilting means comprise a support frame 81 which carries table 31 and the associated means for rotating table 31 around the rotating axis. As schematically shown in FIG. 10, support frame 81 is rotatably mounted on supports 82 and 83, and a motor 84 and mechanical transmission elements 85 and 86 rotate support frame 81 about axis 29 of a desired angle and thereby modify the tilting angle of table 31.

If the method according to the invention is not performed on a plurality samples on a multiple-sample holder 12, but on a single sample contained in a sample container 11, the apparatus required for positioning, rotating and tilting the sample container is much smaller than the one described above and comprises a sample container holder instead of table 31 and electromechanical means for positioning, rotating and tilting the sample holder.

Multiple-sample holder 12 comprises, for example, a matrix array of holes adapted for receiving respective sample containers 11 having the above-described structure.

Substrate 19 is, for example, as described above with reference to FIGS. 1 to 5. Substrate may be a plane wall or foil. Substrate 19 is, for example, the bottom wall 19 of sample container, for example, of a sample container 11, which has, for example, a cylindrical side wall 18 and which has an upper opening.

As already described with reference to FIGS. 1-4, in the embodiment shown by FIG. 10, strip-shaped X-ray beam 24 illuminates a line segment 40 which is oriented in the direction of tilting axis 28. Line segment 40 may coincide with tilting axis 28 and extend between points A and B shown in FIGS. 1, 2 and 3. In one embodiment, the length of line segment 40 is adjusted to be equal to or approximately equal to the inner diameter of the sample container.

When substrate 19 is in the initial position, the central axis of beam 24 and rotation axis 29 pass through the center 17 of substrate 19.

In an embodiment, detector 22 is a movable detector. In another embodiment, detector 22 is a stationary detector which lies in a portion of a spherical surface.

In a further embodiment of the apparatus, the means for moving sample substrate 19 are adapted for effecting a rotation of substrate 19 covering an angle which is equal to or close to 360 degrees. In another embodiment, the rotation of substrate 19 covers an angle which is less than 360 degrees. In yet another embodiment, the rotation of substrate 19 covers an angle which is greater than 360 degrees.

In the embodiment shown in FIG. 10, the apparatus also comprises means for focusing X-ray beam 24, for example, a Germanium (111) monochromator 23 that is located in the path of beam 24 and between X-ray source 21 and pre-selected substrate 19 which holds the sample to be analyzed.

In one embodiment the radiation source 21 and thereby beam 24 are stationary, and pre-selected substrate 19 is moved with respect to beam 24.

MEASUREMENT RESULTS

The X-ray diffractograms shown by FIGS. 11-15 were obtained with the methods of transmission mode X-ray diffraction analysis and apparatuses therefor. These are diffractograms obtained for one and the same compound under different measurement conditions. In FIGS. 11-15 the vertical axis shows a parameter corresponding to the intensity of the diffracted beam in arbitrary units (abbreviated a.u.).

Figure 11:
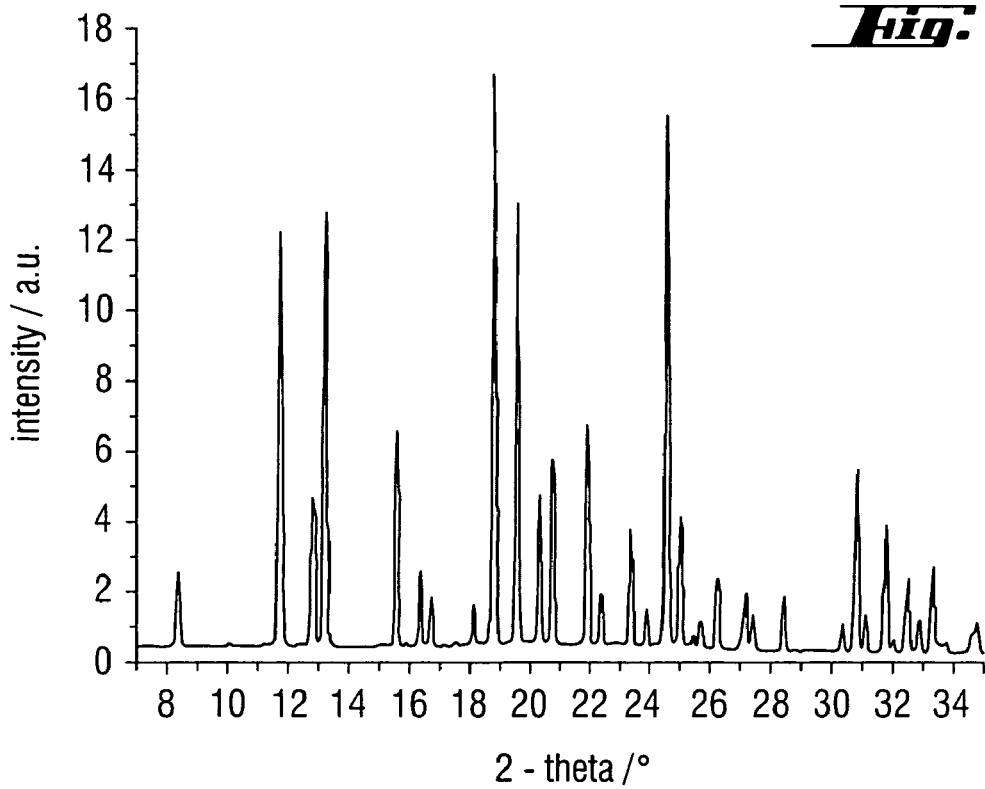
FIG. 11 shows an X-ray diffraction pattern which serves as reference for evaluating the quality of diffraction patterns obtained with different methods.

As basis for evaluating the results with the methods of transmission mode X-ray diffraction analysis and apparatuses therefor, the reference diffractogram shown by FIG. 11 was obtained by measuring a sample in powder form contained in a capillary tube. The diffractograms shown by FIGS. 12-15 were obtained for one and the same sample of the compound having the diffractogram shown by FIG. 11.

FIG. 11 shows an X-ray diffraction pattern which serves as reference for evaluating the quality of diffraction patterns obtained with different methods.

Figure 12:
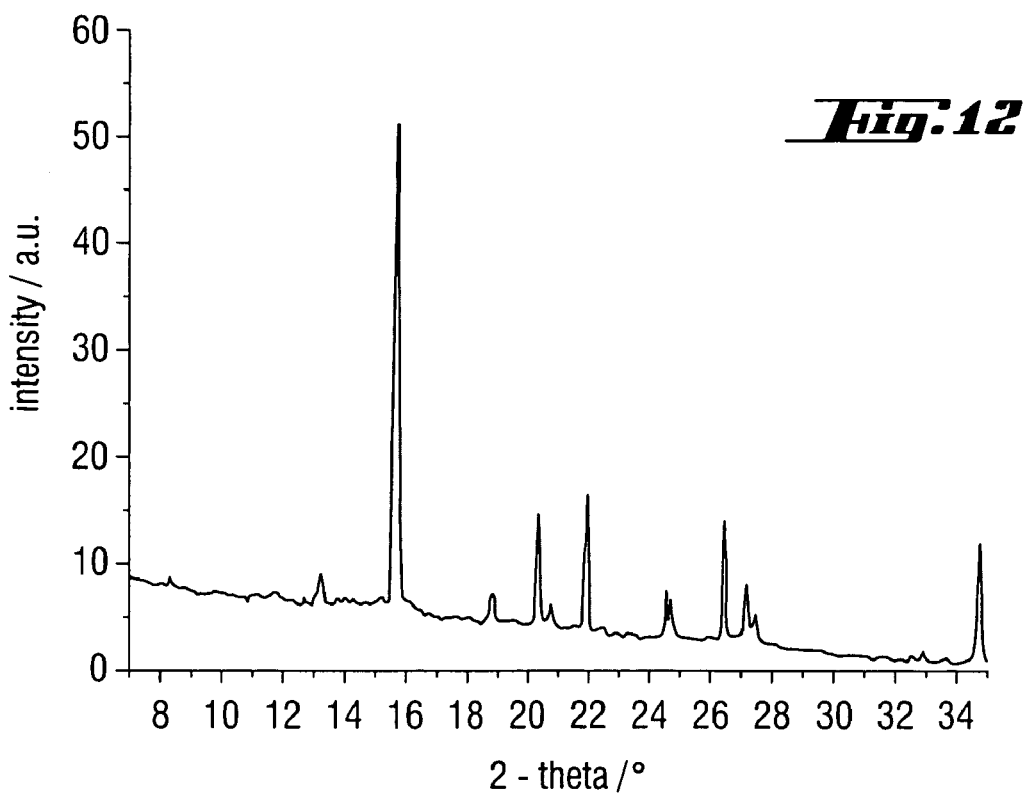
FIG. 12 shows an X-ray diffraction pattern obtained with a stationary sample.

FIG. 12 shows an X-ray diffraction pattern obtained with a stationary sample. Compared with the diffractogram of FIG. 11, the diffractogram of FIG. 12 has much less diffracted peaks of radiation, and some of these peaks have intensities which are disproportionately strong.

Figure 13:
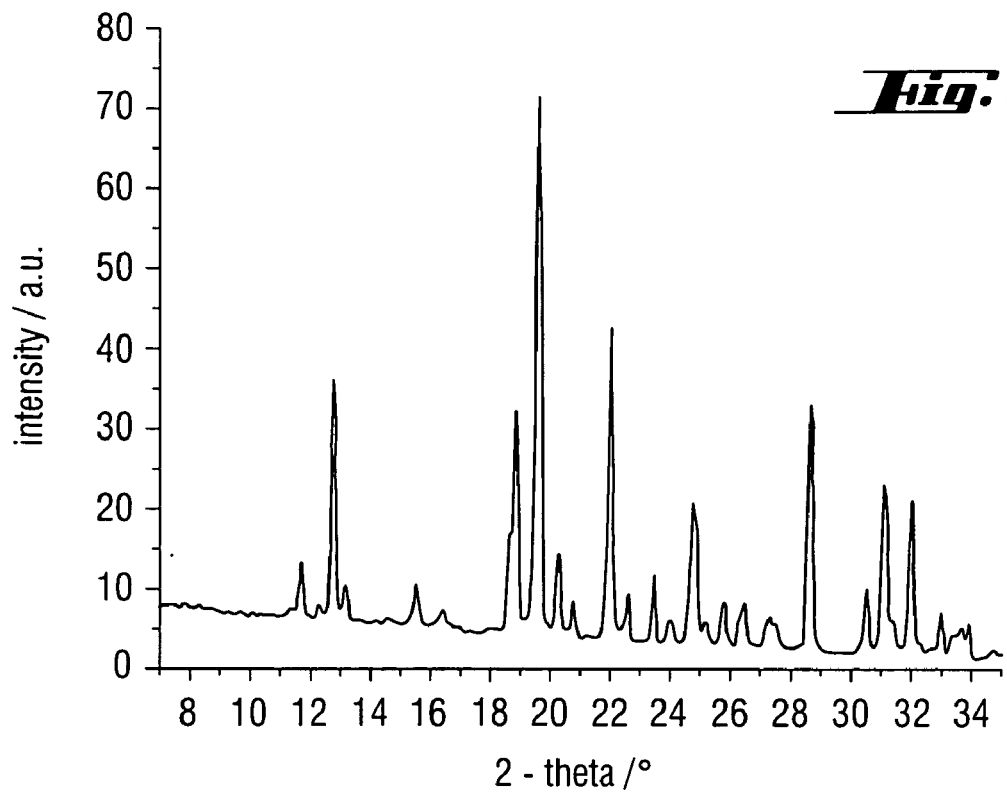
FIG. 13 shows an X-ray diffraction pattern obtained with a sample that is rotated 360 degrees during the detection of the radiation diffracted by a sample.

FIG. 13 shows an X-ray diffraction pattern obtained with a sample that is rotated 360 degrees during the detection of the radiation diffracted by a sample, but that is not tilted. Compared with the diffractogram of FIG. 12, the diffractogram of FIG. 13 has substantially more diffracted peaks of radiation, but not as many as the reference diffractogram of FIG. 11. In addition, the intensity relationship of the peaks in FIG. 13 differ from the intensity relationship of the peaks in the reference diffractogram of FIG. 11.

Figure 14:
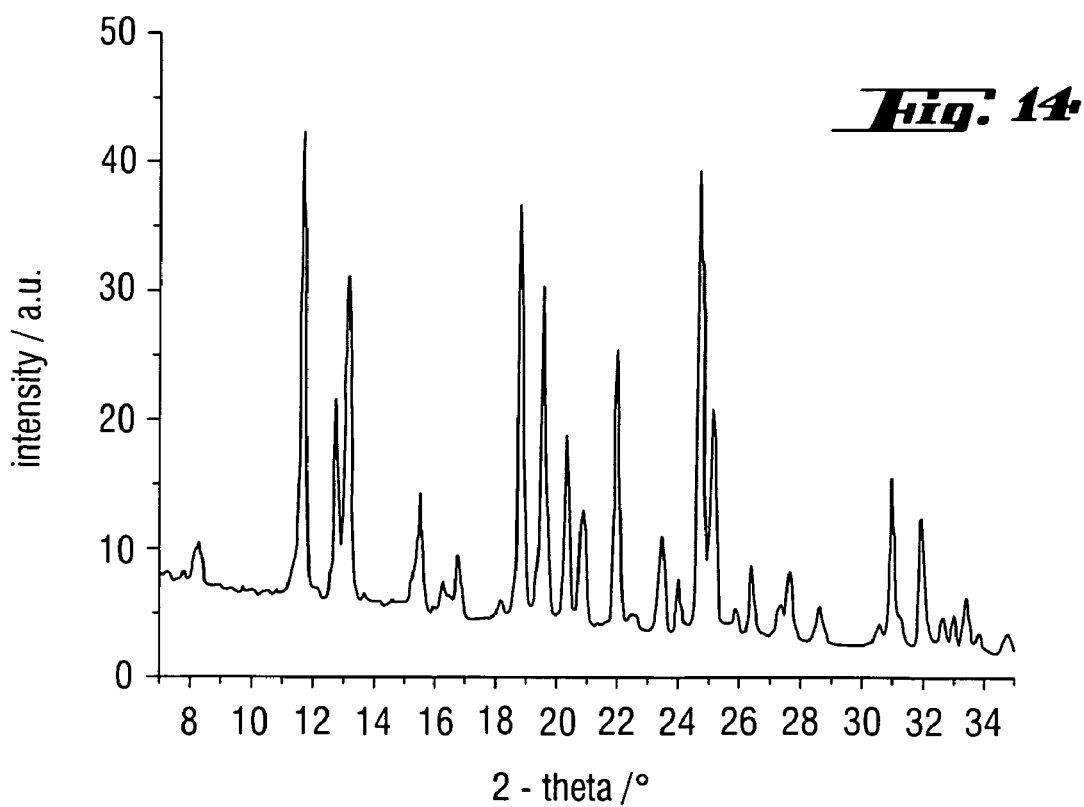
FIG. 14 shows an X-ray diffraction pattern obtained with a sample that is tilted over a certain tilting angle and rotated 360 degrees during the detection of the radiation diffracted by a sample.

FIG. 14 shows an X-ray diffraction pattern obtained with a sample that is tilted over a certain tilting angle and rotated 360 degrees during the detection of the radiation diffracted by a sample. The diffracted peaks of radiation of this diffractogram correspond closely to those of the peaks of the reference diffractogram of FIG. 11.

Figure 15:
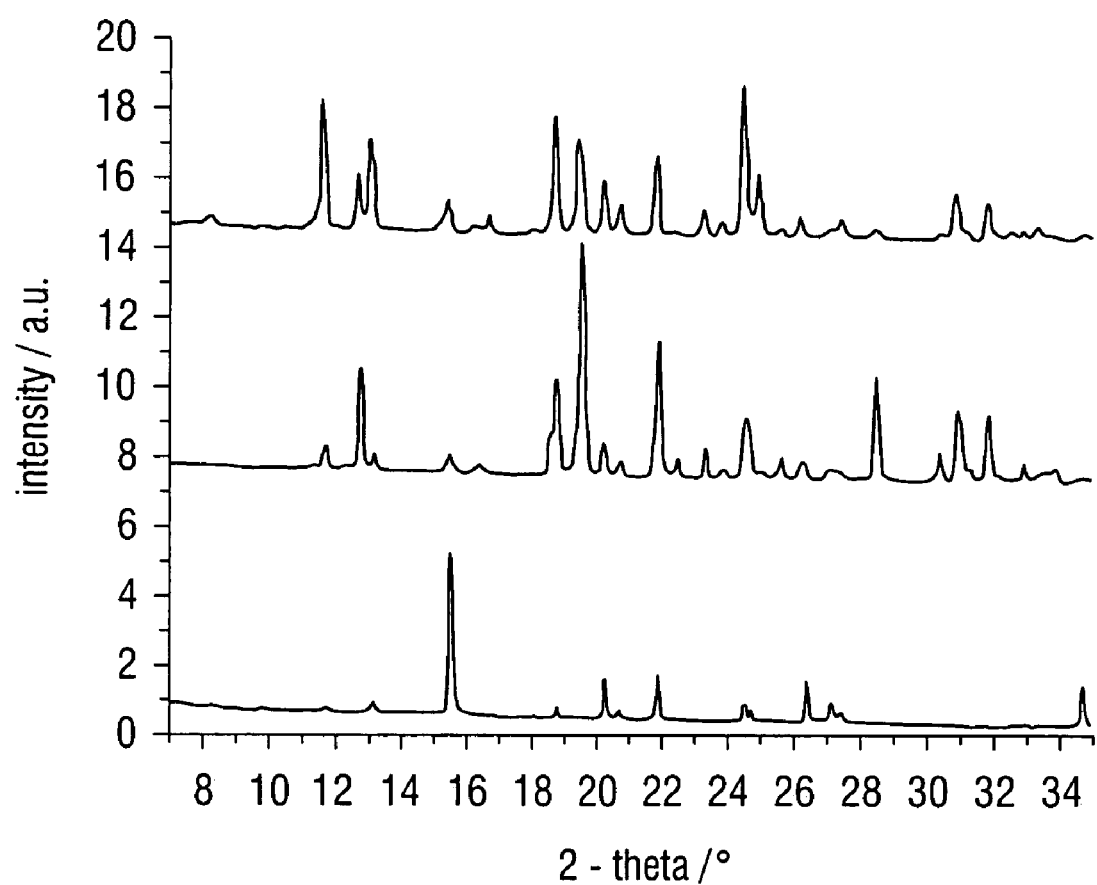
FIG. 15 shows three X-ray diffraction patterns obtained under the following conditions: the lower diffraction pattern is obtained with a stationary sample, the diffraction pattern in the center is obtained when the sample is rotated only during the measurement, the upper diffraction pattern is obtained with a sample that is rotated and tilted during the measurement.

FIG. 15 shows for the purpose of comparison three X-ray diffraction patterns obtained under the following conditions. The lower diffraction pattern in FIG. 15 is obtained with a stationary sample as for the obtention of the diffractogram of FIG. 12. The diffraction pattern in the center of FIG. 15 is obtained when the sample is only rotated but not tilted during the measurement, as for the obtention of the diffractogram of FIG. 13. The upper diffraction pattern in FIG. 15 is obtained with a sample that is rotated and tilted during the measurement, as for the obtention of the diffractogram of FIG. 14.

Although embodiments of the invention have been described using specific terms, such description is for illustrative purposes only, and it is to be understood that changes and variations may be made without departing from the spirit or scope of the following claims.

The invention claimed is:

1. A method of transmission mode X-ray diffraction analysis, comprising the steps of:
   (a) placing a sample to be analyzed on a substrate that is transparent to X-ray radiation and that is adapted for receiving and holding the sample,
   (b) generating X-ray radiation by means of an X-ray radiation source that generates a strip-shaped X-ray beam with a central part that extends along a path in a plane,
   (c) positioning the substrate and thereby the sample in an initial position in which the sample lies in the path of the strip-shaped X-ray beam whereby a slice of the sample is irradiated by the strip-shaped X-ray beam,
   (d) rotating the substrate and thereby the sample with respect to the initial position around a rotation axis over a predetermined rotation angle during a time interval, wherein the rotation axis is perpendicular to the substrate,
   (e) tilting the substrate and thereby the sample during the time interval, said tilting being with respect to the initial position and around a tilting axis perpendicular to the rotation axis over a tilting angle that the rotation axis forms with the plane through which the central part of the strip-shaped X-ray beam extends, wherein the tilting angle varies between a first predetermined value and a second predetermined value,
   (f) detecting with a detector the X-ray radiation transmitted through and diffracted by the sample during the time interval, and
   (g) analyzing the X-ray radiation that is detected.

2. The method according to claim 1, wherein the rotating and tilting of the substrate are simultaneous and continuous.

3. The method according to claim 1, wherein the tilting of the substrate is performed in steps and the rotating of the substrate is over a predetermined rotation angle for each step.

4. The method according to claim 1, wherein the substrate is a planar substrate.

5. The method according to claim 1, wherein the substrate has a center and the central part of the strip-shaped X-ray beam and the rotation axis pass through the center of the substrate when the substrate is in the initial position.

6. The method according to claim 1, wherein the X-ray radiation source is stationary.

7. The method according to claim 1, wherein the predetermined rotation angle is equal to or approximately equal to 360 degrees.

8. The method according to claim 1, wherein the predetermined rotation angle is less than 360 degrees.

9. The method according to claim 1, wherein the predetermined rotation angle is greater than 360 degrees.

10. The method according to claim 1, wherein the strip-shaped X-ray beam illuminates a line segment having a length that lies substantially along the tilting axis.

11. The method according to claim 10 further comprising inserting a sample into a sample container having an inner diameter, wherein the length of the line segment is equal to or approximately equal to the inner diameter of the sample container and wherein the substrate forms part of the sample container.

12. An apparatus for transmission mode X-ray diffraction analysis, comprising:
    (a) a source of X-ray radiation that generates X-ray radiation having a strip-shaped X-ray beam with a central part that extends along a plane,
    (b) a substrate transparent to X-ray radiation and adapted for receiving a sample,
    (c) means for positioning the substrate in an initial position at which the sample located on the substrate lies in the path of the strip-shaped X-ray beam,
    (d) means for rotating the substrate and thereby the sample on it around a rotation axis over a predetermined rotation angle, wherein the rotation axis is perpendicular to the substrate,
    (e) means for tilting the substrate over a tilting angle around a tilting axis that is perpendicular to the rotation axis, and
    (f) a detector for detecting the X-ray radiation that is transmitted through and diffracted by the sample.

13. The apparatus according to claim 12, wherein the substrate is a planar substrate.

14. The apparatus according to claim 13 further comprising a sample container for holding the sample, the sample container having a bottom wall, wherein the planar substrate is the bottom wall of the sample container.

15. The apparatus according to claim 14, wherein the sample container and the strip-shaped X-ray beam each have a width, wherein the width of the sample container is approximately equal to the width of the strip-shaped X-ray beam.

16. The apparatus according to claim 12, wherein the substrate has a center and the central part of the strip-shaped X-ray beam and the rotation axis pass through the center of the substrate when the substrate is in the initial position.

17. The apparatus according to claim 12, wherein the detector is a movable detector.

18. The apparatus according to claim 12, wherein the detector is a stationary detector.

19. The apparatus according to claim 14, wherein the strip-shaped X-ray beam defines a path, and the apparatus further comprises first focusing means located in the path of the strip-shaped X-ray beam between the source of X-ray radiation and the substrate.

20. The apparatus according to claim 12, wherein the source of X-ray radiation is stationary.

21. The apparatus according to claim 12, wherein the predetermined rotation angle is equal to or approximately equal to 360 degrees.

22. The apparatus according to claim 12, wherein the predetermined rotation angle is less than 360 degrees.

23. The apparatus according to claim 12, wherein the predetermined rotation angle is greater than 360 degrees.

24. The apparatus according to claim 19, wherein the first focusing means focuses the strip-shaped X-ray beam in a line segment having a length that lies substantially along the tilting axis.

25. The apparatus according to claim 24, wherein the sample container has an inner diameter and the length of the line segment is adjusted to be equal to or approximately equal to the inner diameter of the sample container.

26. A method of transmission mode X-ray diffraction analysis, comprising the steps of:
    (a) placing a plurality of samples to be analyzed on a corresponding plurality of substrates of a sample holder, wherein each of the plurality of substrates is transparent to X-ray radiation,
    (b) generating X-ray radiation by means of an X-ray radiation source that generates a strip-shaped X-ray beam with a central part that extends along a path in a plane,
    (c) placing the sample holder in an apparatus comprising means for moving and positioning the sample holder so that a pre-selected sample can be positioned in the path of the strip-shaped X-ray beam,
    (d) positioning the pre-selected sample and a corresponding pre-selected substrate in an initial position in which the pre-selected sample lies in the path of the strip-shaped X-ray beam whereby a slice of the pre-selected sample is irradiated by the strip-shaped X-ray beam,
- (e) rotating the pre-selected substrate and thereby the pre-selected sample with respect to the initial position around a rotation axis over a predetermined rotation angle during a time interval, wherein the rotation axis is perpendicular to the substrate,
- (f) tilting, during the time interval, the pre-selected substrate and thereby the pre-selected sample during the time interval, said tilting being with respect to the initial position and around a tilting axis perpendicular to the rotation axis over a tilting angle that the rotation axis forms with the plane through which the central part of the strip-shaped X-ray beam extends, wherein the tilting angle varies between a first predetermined value and a second predetermined value,
- (g) detecting with a detector X-ray radiation transmitted through and diffracted by the pre-selected sample during the time interval, and
- (h) analyzing the X-ray radiation that is detected.

27. The method according to claim 26, wherein the rotating and tilting of the pre-selected substrate are simultaneous and continuous.

28. The method according to claim 26, wherein the tilting of the pre-selected substrate is performed in steps and the rotating of the pre-selected substrate is over a predetermined rotation angle for each step.

29. The method according to claim 26, wherein the plurality of substrates are planar substrates.

30. The method according to claim 26, wherein the plurality of substrates each have a center and the central part of the strip-shaped X-ray beam and the rotation axis pass through the center of the pre-selected substrate when the pre-selected substrate is in the initial position.

31. The method according to claim 26, wherein the X-ray radiation source is stationary.

32. The method according to claim 26, wherein the predetermined rotation angle is equal to or approximately equal to 360 degrees.

33. The method according to claims 26, wherein the predetermined rotation angle is less than 360 degrees.

34. The method according to claim 26, wherein the predetermined rotation angle is greater than 360 degrees.

35. The method according to claim 26, wherein the strip-shaped X-ray beam is focused in a line segment having a length that lies substantially along the tilting axis (28).

36. The method according to claim 26 further comprising repeating steps (d), (e), (f), (g) and (h) for each of the plurality of samples in the sample holder.

37. An apparatus for transmission mode X-ray diffraction analysis, comprising:
- (a) a source of X-ray radiation that generates X-ray radiation having a strip-shaped X-ray beam with a central part that extends along a plane,
- (b) a sample holder comprising a plurality of substrates transparent to X-ray radiation, wherein each of the substrates is adapted for receiving a sample to be analyzed,
- (c) means for positioning a preselected substrate and thereby a sample on that substrate in an initial position at which the sample lies in the path of the strip-shaped X-ray beam,
- (d) means for rotating the preselected substrate and thereby the sample on that substrate around a rotation axis over a predetermined rotation angle, wherein the rotation axis is perpendicular to the substrate,
- (e) means for tilting the preselected substrate and thereby the sample on that substrate over a tilting angle around a tilting axis that is perpendicular to the rotation axis, and
- (f) a detector for detecting the X-ray radiation that is transmitted through and diffracted by each sample.

38. The apparatus according to claim 37, wherein each substrate is a planar substrate.

39. The apparatus according to claim 38 further comprising a plurality of sample containers for holding the plurality of samples within the sample holder, wherein each sample container has a bottom wall and each planar substrate is the bottom wall of a corresponding sample container.

40. The apparatus according to claim 39, wherein each sample container and the strip-shaped X-ray beam have a width, wherein the width of each sample container is approximately equal to the width of the strip-shaped X-ray beam.

41. The apparatus according to claim 37, wherein each substrate has a center and the central part of the strip-shaped X-ray beam and the rotation axis pass through the center of each substrate when the substrate is in the initial position.

42. The apparatus according to claim 37, wherein the detector is a movable detector.

43. The apparatus according to claim 37, wherein the detector is a stationary detector.

44. The apparatus according to claim 37, wherein the strip-shaped X-ray beam defines a path, and the apparatus further comprises first focusing means located in the path of the strip-shaped X-ray beam between the source of X-ray radiation and each substrate when each substrate is in the initial position.

45. The apparatus according to claim 37, wherein the source of X-ray radiation is stationary.

46. The apparatus according to claim 37, wherein the predetermined rotation angle is equal to or approximately equal to 360 degrees.

47. The apparatus according to claim 37, wherein the predetermined rotation angle is less than 360 degrees.

48. The apparatus according to claim 37, wherein the predetermined rotation angle is greater than 360 degrees.

49. The apparatus according to claim 44, wherein the first focusing means focuses the strip-shaped X-ray beam in a line segment having a length that lies substantially along the tilting axis.

50. The apparatus according to claim 49, wherein the preselected sample container has an inner diameter and the length of the line segment is adjusted to be equal to or approximately equal to the inner diameter of the pre-selected sample container.

* * * * *